United States Patent [19]

Badylak et al.

[11] Patent Number: 5,281,422
[45] Date of Patent: Jan. 25, 1994

[54] GRAFT FOR PROMOTING AUTOGENOUS TISSUE GROWTH

[75] Inventors: Stephen F. Badylak; Leslie A. Geddes, both of W. Lafayette; K. Donald Shelbourne, Indianapolis; Gary C. Lantz, Lafayette; Arthur C. Coffey, Indianapolis, all of Ind.

[73] Assignee: Purdue Research Foundation, West Lafayette, Ind.

[21] Appl. No.: 764,818

[22] Filed: Sep. 24, 1991

[51] Int. Cl.$^5$ .............................................. A61K 35/38
[52] U.S. Cl. ..................................... 424/551; 623/11; 623/13
[58] Field of Search ..................... 424/551; 623/11, 13

[56] References Cited

U.S. PATENT DOCUMENTS 4,902,508  2/1990  Badylak et al. ..................... 424/551
4,956,178  9/1990  Badylak et al. ..................... 424/551

OTHER PUBLICATIONS

*Comparison of Bovine Collagen Xenografts to Autografts in the Rabbit*, J. C. Tauro, et al., *Clinical Orthopaedics and Related Research*, No. 266, May, 1991, pp. 271–284.

*Development of a Reconstituted Collegen Tendon Prosthesis*, Jack D. Goldstein, et al. *The Journal of Bone and Joint Surgery, Incorporated*, vol. 71-A, No. 8, Sep. 1989, pp. 1183–1191.

"Aortic Replacement With Multi-Layer Submucosa Prostheses Made From Heterologous Small Intestine", G. Rotthoff, et al., *J. Cardiovas. Sur.*, pp. 31–35.

"Replacement Of The Abdominal Aorta By An Ileum Muscle Tube In An Animal Experiment", J. Huth, et al., *Thoraxchir. Vask. Chir.*, 15(4): 401–407, Aug. 1967.

"Long Term Observations And Histological Studies On Vessel And Heart Wall Grafts From Small Intestine", R. Haring, et al., *Langenbecks Arch. Klin. Chir.*, 1965, 313:664–8.

"Replacement Of The Abdominal Aorta With A Small-Intestine Muscle Tube In An Animal Experiment", J. Huth, *Zentralbl. Chir.*, 1817–19 (1967).

"Reconstruction Of The Arterial Flow Path By Autologous Intestinal Muscle Grafts In The Dog", Bruch, et al., *Folia Angiologica*, vol. 29 (3–5/81) pp. 65–68.

"Replacement Of The Aorta By Multilayered Submucosa Prostheses Of Heterologous Ileum", G. Rotthoff, et al., *Bulletin De La Societe International de Chirurgia*, No. 2, 1969, 256–259.

"Replacement of Dog's Aorta by Autologous Intestinal Muscle in the Infected Retroperitoneum", R. Broll, et al., *Eur. Surg. Res.*, 18:390–395 (1985).

*Primary Examiner*—Douglas W. Robinson
*Assistant Examiner*—Jean C. Witz
*Attorney, Agent, or Firm*—Barnes & Thornburg

[57] ABSTRACT

Surgical repair of diseased or damaged endogenous connective tissue can be accomplished using a tissue graft formed from a delaminated segment of intestinal tissue. The tissue graft comprises the intestinal tunica submucosa, muscularis mucosa and stratum compactum delaminated from the tunica muscularis and the luminal portion of the tunica mucosa. The graft can be conditioned by stretching and formed as a multilayer composition for high tensile strength and resistance to tearing at its points of attachment to existing physiological structures.

13 Claims, 3 Drawing Sheets

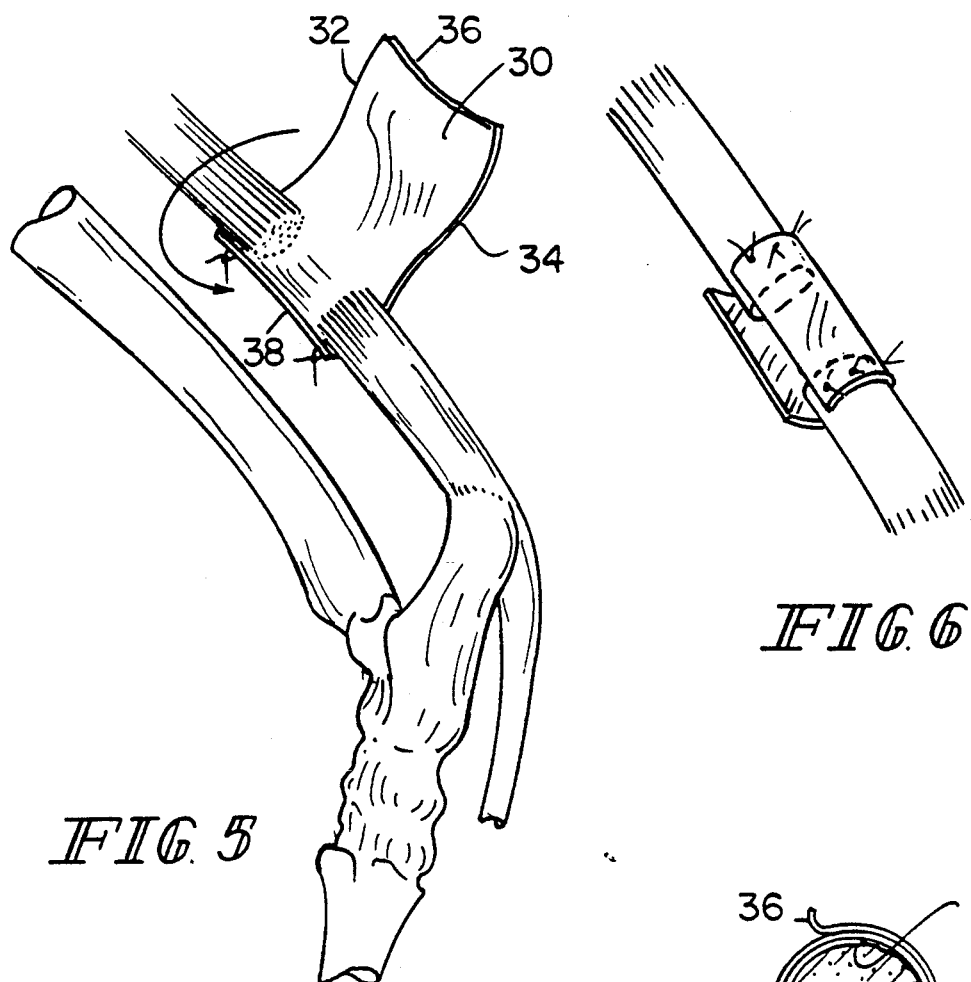
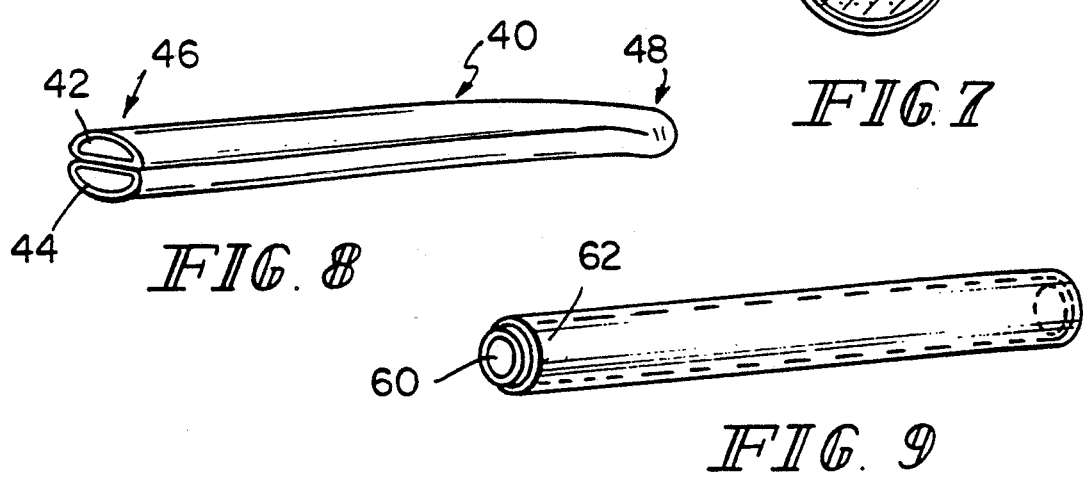

GRAFT FOR PROMOTING AUTOGENOUS TISSUE GROWTH

FIELD OF THE INVENTION

This invention relates to novel tissue graft constructs and their use to promote regrowth and healing of damaged or diseased tissue structures. More particularly this invention is directed to use of intestinal tissue grafts as connective tissue substitutes, and most particularly to their use in surgical repair of ligaments and tendons and for their use as a surgically applied bone wrap to promote healing of bone fractures.

BACKGROUND AND SUMMARY OF THE INVENTION

Researchers in the surgical arts have been working for many years to develop new techniques and materials for use as grafts to replace or repair damaged or diseased tissue structures, particularly bones and connective tissues, such as ligaments and tendons, and to hasten fracture healing. It is very common today, for instance, for an orthopaedic surgeon to harvest a patellar tendon of autogenous or allogenous origin for use as a replacement for a torn cruciate ligament. The surgical methods for such techniques are well known. Further it has become common for surgeons to use implantable prostheses formed from plastic, metal and/or ceramic material for reconstruction or replacement of physiological structures. Yet despite their wide use, surgically implanted prostheses present many attendant risks to the patient. It will suffice to say that surgeons are in need of a non-immunogenic, high tensile strength graft material which can be used for surgical repair of bones, tendons, ligaments and other functional tissue structures.

Researchers have been attempting to develop satisfactory polymer or plastic materials to serve as ligament, or tendon replacements or as replacements for other connective tissues, such as those involved in hernias and joint-dislocation injuries. It has been found that it is difficult to provide a tough, durable plastic material which is suitable for long-term connective tissue replacement. Plastic materials can become infected and difficulties in treating such infections often lead to graft failure.

In accordance with the present invention there is provided tissue graft constructs for orthopaedic and other surgical applications which in experiments to date have been shown to exhibit many of the desirable characteristics important for optimal graft function.

The graft construct in accordance with this invention is prepared from a delaminated segment of intestinal tissue of a warm-blooded vertebrate, the segment comprising the tunica submucosa, the muscularis mucosa and the stratum compactum of the tunica mucosa. The tunica submucosa, muscularis mucosa and stratum compactum are delaminated from the tunica muscularis and the luminal portion of the tunica mucosa of the segment of intestinal tissue. The resulting segment is a tubular, very tough, fibrous, collagenous material which is fully described in U.S. Pat. No. 4,902,508 issued Feb. 20, 1990 and U.S. Pat. No. 4,956,178 issued Sep. 11, 1990, which patents are expressly incorporated herein by reference. In those patents, the tissue graft material is primarily described in connection with vascular graft applications.

Intestinal submucosa graft material may be harvested from a biological source such as animals raised for meat production, including, for example, pigs, cattle and sheep or other warm-blooded vertebrates. Older sows having a weight between 400 and 600 lbs. have been found to be particularly good sources of graft material for use for this invention. A graft segment removed from such an older sow can have a tensile strength of up to 1700 psi in the longitudinal direction of the intestine. Thus, there is a ready source of intestinal submucosa graft material in slaughter houses around the country, ready to be harvested and utilized in accordance with the present invention.

The tri-layer intestinal segments used to form the graft constructs in accordance with this invention can be used in their delaminate tubular form or they can be cut longitudinally or laterally to form elongated tissue segments. In either form, such segments have an intermediate portion and opposite end positions and opposite lateral portions which can be formed for surgical attachment to existing physiological structures, using surgically acceptable techniques.

An advantage of the intestinal submucosa graft formed for surgical repair in accordance with the present invention is its resistance to infection. The intestinal submucosa graft material, fully described in the aforesaid patents, have high infection resistance, long shelf life and storage characteristics. It has been found that xenogeneic intestinal submucosa is compatible with hosts following implantation as vascular grafts, ligaments and tendons because of its basic composition. The intestinal submucosa connective tissue is apparently very similar among species. It is not recognized by the host's immune system as "foreign" and therefore is not rejected. Further the intestinal submucosa grafts appear to be extremely resistant to infection because of their trophic properties toward vascularization and toward endogenous tissues surgically affixed or otherwise associated with the implant graft. In fact, most of the studies made with intestinal submucosa grafts to date have involved non-sterile grafts, and no infection problems have been encountered. Of course, appropriate sterilization techniques acceptable to the Federal Drug Administration (FDA) may well be used to treat grafts in accordance with the present invention.

It has been found that unsterilized clean intestinal submucosa graft material can be kept at 4° C. (refrigerated) for at least one month without loss of graft performance. When the intestinal submucosa graft material is sterilized by known methods, it will stay in good condition for at least two months at room temperature without any resultant loss in graft performance.

It has also been found that the grafts formed and used in accordance with this invention upon implantation undergo biological remodelling. They serve as a rapidly vascularized matrix for support and growth of new endogenous connective tissue. The graft material used in accordance with this invention has been found to be trophic for host tissues with which it is attached or otherwise associated in its implanted environment. In multiple experiments the graft material has been found to be remodelled (resorbed and replaced with autogenous differentiated tissue) to assume the characterizing features of the tissue(s) with which it is associated at the site of implantation. In tendon and ligament replacement studies the graft appears to develop a surface that is synovialized. Additionally, the boundaries between the graft and endogenous tissue are no longer discernible. Indeed, where a single graft "sees" multiple microenvironments as implanted, it is differentially remodeled along its length. Thus when used in cruciate ligament replacement experiments not only does the portion of the graft traversing the joint become vascularized and actually grow to look and function like the original ligament, but the portion of the graft in the femoral and tibial bone tunnels rapidly incorporates into and promotes development of the cortical and cancellous bone in those tunnels. In fact, it has been found that after six months, it is not possible to identify the tunnels radiographically. It appears that intestinal submucosa serves as a matrix for and stimulates bone regrowth (remodeling) within the tunnels. The bone tunnels with the encompassed intestinal submucosa graft have never been shown to be a weak point in the tensile-strength evaluations after sacrifice of test dogs accomplished to date.

It is one object of the present invention, therefore, to provide graft constructs for use as connective tissue substitute, particularly as a substitute for ligaments and tendons. The graft is formed from a segment of intestinal tissue of a warm-blooded vertebrate. The graft construct comprises the tunica submucosa, the muscularis mucosa and the stratum compactum of the tunica mucosa, said tunica submucosa, muscularis mucosa and stratum compactum being delaminated from the tunica muscularis and the luminal portions of the tunica mucosa of the segment of intestinal tissue. The graft construct has a longitudinal dimension corresponding to the length of the segment of intestinal tissue and a lateral dimension proportioned to the diameter of the segment of intestinal tissue. For tendon and ligament replacement, applications the resulting segment is typically preconditioned by stretching longitudinally to a length longer than the length of the intestinal tissue segment from which it was formed. For example, the segment is conditioned by suspending a weight from said segment, for a period of time sufficient to allow about 10 to about 20% elongation of the tissue segment. Optionally, the graft material can be preconditioned by stretching in the lateral dimension. (The graft material exhibits similar viscoelastic properties in the longitudinal and lateral dimensions). The graft segment is then formed in a variety of shapes and configurations, for example, to serve as a ligament or tendon replacement or substitute or a patch for a broken or severed tendon or ligament. Preferably, the segment is shaped and formed to have a layered or even a multilayered configuration with at least the opposite end portions and/or opposite lateral portions being formed to have multiple layers of the graft material to provide reinforcement for attachment to physiological structures, including bone, tendon, ligament, cartilage and muscle. In a ligament replacement application, opposite ends are attached to first and second bones, respectively, the bones typically being articulated as in the case of a knee joint. It is understood that ligaments serve as connective tissue for bones, i.e.. between articulated bones, while tendons serve as connective tissue to attach muscle to a bone.

When a segment of intestine is first harvested and delaminated as described above, it will be a tubular segment having an intermediate portion and opposite end portions. The end portions are then formed, manipulated or shaped to be attached, for example, to a bone structure in a manner that will reduce the possibility of graft tearing at the point of attachment. Preferably it can be folded or partially everted to provide multiple layers for gripping, for example, with spiked washers or staples. Alternatively, the segment may be folded back on itself to join the end portions to provide a first connective portion to be attached, for example, to a first bone and a bend in the intermediate portion to provide a second connective portion to be attached to a second bone articulated with respect to the first bone.

For example, one of the end portions may be adapted to be pulled through a tunnel in, for example, the femur and attached thereto, while the other of the end portions may be adapted to be pulled through a tunnel in the tibia and attached thereto to provide a substitute for the natural cruciate ligament, the segment being adapted to be placed under tension between the tunnels to provide a ligament function, i.e., a tensioning and positioning function provided by a normal ligament.

The intestinal submucosa segment, which in its preferred embodiment consists essentially of the tunica submucosa, muscularis mucosa and stratum compactum, has been found to have good mechanical strength characteristics in the same delaminated tubular form in which it is produced following the described delamination procedure. It has been found that having the stratum compactum layer inside the tubular form in a tendon or ligament graft provides good trophic properties for vascularization. It is believed that grafts used in accordance with the present invention with the intestinal segment inverted, i.e., with the stratum compactum on the outside will exhibit like functionality, but further testing is required to determine the vascularization characteristics with that structure utilized, for example, as a tendon or ligament graft.

Another object of the present invention is to provide a method for surgical repair of diseased or damaged tissues connecting first and second tissues structures selected from the group consisting of bone, ligament, tendon, cartilage and muscle. The method comprises the step of attaching the first and second structures to opposite end portions or opposite lateral portions of a tissue graft construct formed in accordance with the above described embodiments. The graft comprises the tunica submucosa, the muscularis mucosa and the stratum compactum of a segment of intestinal tissue of a warm-blooded vertebrate, said tunica submucosa, muscularis mucosa and stratum compactum being delaminated from the tunica muscularis and the luminal portion of the tunica mucosa of said intestinal tissue.

Because grafts used in orthopaedic applications are typically placed under tension in their surgical installation, it may be preferable to combine two or even more tissue segments to provide a multi-ply (multi-layered) graft construct. It is another object of the present invention, therefore, to provide such grafts in which two or more intestinal segments are arranged to have their end portions joined together with the joined end portions and/or lateral portions adapted to be attached to a bone, tendon, ligament or other physiological structure. One method for providing a double intestinal segment may be to pull one tubular segment internally within another segment to provide a double-walled tube, the joined ends of which can be attached, for example, to a bone, tendon or ligament. These doubled segments will provide enhanced tensile strength and resistance to stretching under tension.

A further object of the present invention is to provide such a graft in which one of said end portions is adapted to be pulled through a tunnel in, for example, the femur and attached thereto and the other of said end portion is adapted to be pulled through a tunnel in the tibia and attached thereto to provide a substitute for the natural cruciate ligament, the segment being adapted to be placed under tension between the tunnels to provide a ligament function. Similar procedures can be employed to provide ligament function to other articulating bones.

Still a further object of the present invention is to provide an orthopaedic graft for use as connective tissue to hold fractured bone pieces together and in proper orientation in the body, the segment being formed to serve as a fracture wrap about segments of fractured bone and to be attached to the bone.

One other object of this invention is to provide a method for promoting the healing and/or regrowth of diseased or damaged tissue structures by surgically repairing such structures with a tissue graft construct prepared from a segment of intestinal submucosal tissue as described above. The implanted graft construct is trophic toward vascularization and differentiated tissue growth and is essentially remodelled to assume the structural and functional characteristics of the repaired structure.

Other objects and features of the present invention will become apparent as this description progresses.

BRIEF DESCRIPTION OF THE DRAWINGS

FIG. 5 is a fragmentary view showing an achilles tendon with a graft placement in accordance with the present invention adapted to join a break in the tendon.

FIG. 6 is a fragmentary perspective view showing the graft of FIG. 5 being attached.

FIG. 7 is a sectional view showing how the graft is wrapped twice about the tendon in FIGS. 5 and 6.

FIG. 8 shows a tubular section of the graft folded back on itself to provide a double thickness of intestinal submucosa segment.

FIG. 9 is a fragmentary perspective view showing a graft segment pulled within another graft segment to provide a double-walled or tube-within-a tube arrangement.

DETAILED DESCRIPTION OF THE INVENTION

The intestinal submucosa graft of the present invention is harvested and delaminated in accordance with the description in the prior U.S. Pat. Nos. 4,956,178 and 4,902,508. An intestinal submucosa segment is thereby obtained.

To date, of course, such grafts have been used only on test animals. The following description is based upon the experimental uses made or contemplated to date.

Figure 1:
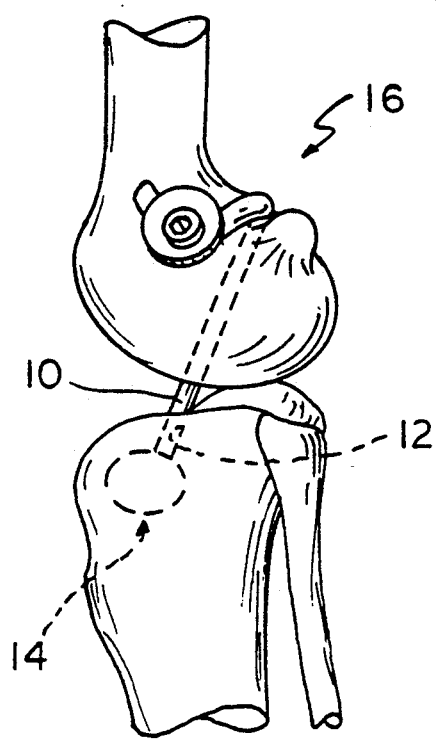
FIG. 1 shows a lateral view of a knee with a graft in accordance with the present invention extending through a tunnel through the tibia and wrapped over the top of a femur.
Figure 2:
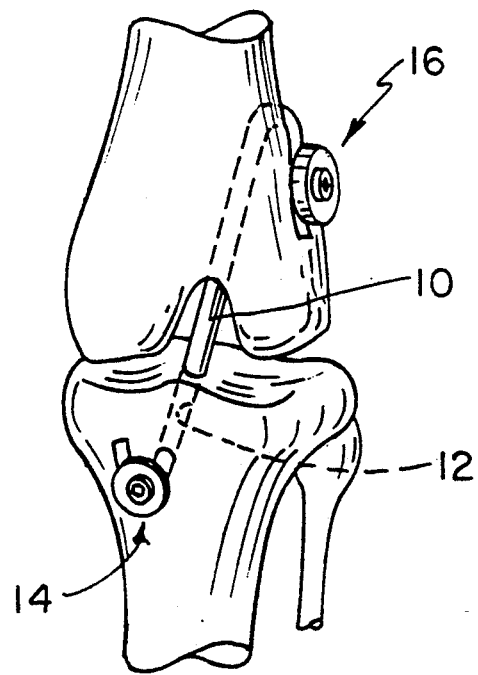
FIG. 2 shows an anterior view of the left stifle showing the graft arrangement of FIG. 1.
Figure 3:
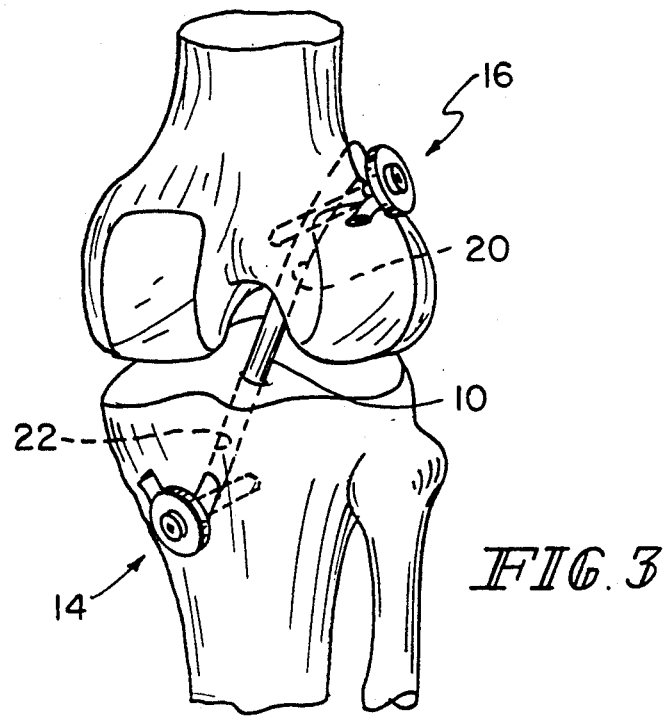
FIG. 3 shows an anterior view of the left stifle with a graft in accordance with the present invention extending through tunnels in both the tibia and the femur with the end portions of the graft attached by screws and spiked washers in accordance with standard orthopaedic surgery practices.

In FIGS. 1 and 2, a femur is shown above the tibia with a lateral view in FIG. 1 and an anterior view of the left stifle in FIG. 2. As best seen in FIG. 2, a graft 10 is installed through a bone tunnel 12 in the tibia in a fashion well-known in orthopaedic surgery. The end portion of the graft 10 is attached as indicated at 14 by a spiked washer and screw arrangement to provide the connection to the tibia. The other end portion of the graft 10 is pulled up through the space between the condylar portions and wrapped over the lateral femoral condyle to be attached as indicated at 16 by another spiked washer and screw arrangement. It will be appreciated that surgeons will generally 14, 16. place such grafts under tension between connections The arrangement shown in FIGS. 1 and 2 may well be more adaptable for testing in dogs than it is for repair of human knees. Thus, FIG. 3 shows a likely human application of the graft 10 extending through aligned tunnels 20, 22 in the femur and tibia with the opposite ends of the graft 10 being connected by teflon spiked washers and screws as indicated at 14 and 16. Such screws and spiked washers may be replaced with spiked bone staples or any other type of soft-tissue-to-bone fixation devices commonly used in orthopaedic surgery. When the graft is pulled through the tunnels 20, 22 and placed under tension by the attachments indicated at 14, 16, the graft serves a ligament function between the femur and tibia. The graft also apparently stimulates bone growth in the tunnels such that the tunnels close in on the grafts to make connections which, after a period of time, do not have to be supplemented by the screw and washer arrangements.

Figure 4:
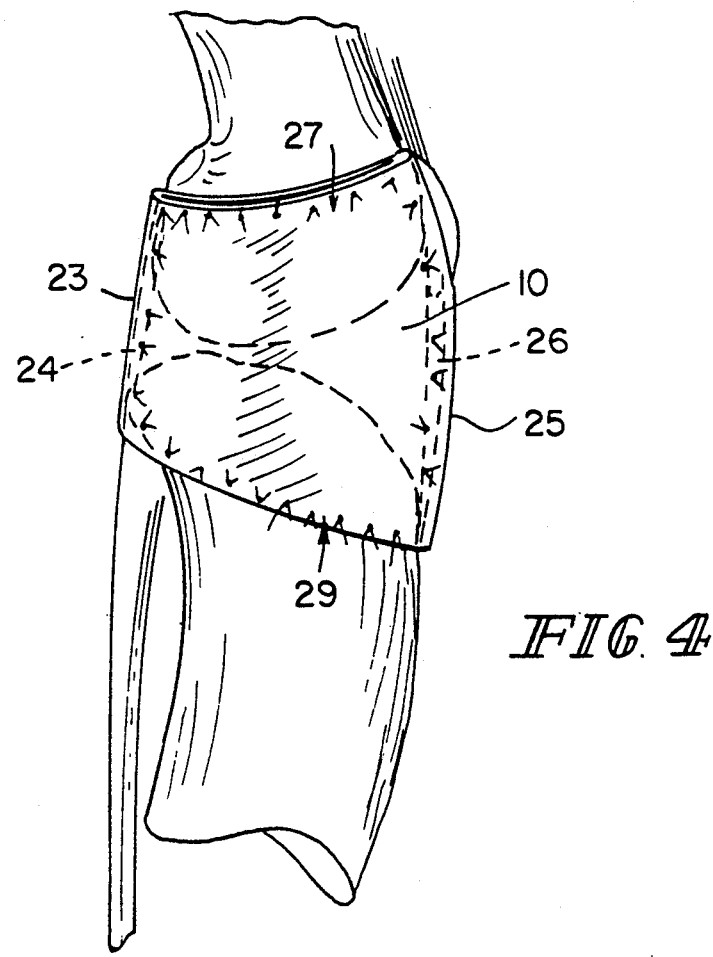
FIG. 4 shows a medial view of the left stifle showing a graft in accordance with the present invention used as a medial collateral ligament replacement with opposite end portions of the graft attached by sutures to existing connective tissues.

FIG. 4 illustrates an intestinal submucosa graft 10 used as a medial collateral ligament replacement attached by sutures to existing adjacent tissues. Thus lateral edges 23,25 of the tubular graft 10 are sutured to the posterior oblique ligament 24 and the patellar tendon 26 while opposite ends 27,29 of graft 10 are sutured to ligament/tendon tissues associated with the femur and tibia, respectively. The graft 10 is preferably placed under moderate tension. As discussed above, the graft may comprise one or more intestinal segments layered together to provide additional strength.

FIGS. 5, 6 and 7 show how a segment of intestinal submucosa 30 may be shaped and formed to connect a broken or severed achilles tendon. The segment 30 is shown as an elongated sheet, its longest dimension corresponding to the longitudinal axis of the intestine from which the segment is removed. The graft segment has generally parallel sides 32, 34 and opposite ends 36, 38. This segment 30 is wrapped about the achilles tendon as shown in FIG. 7 to provide a double wrap or multilayered intermediate portion with the sides 32, 34 providing multiple layer opposite end portions for attachment to the enclosed tendon. The manner in which the graft is sutured to the tendon is illustrated in FIG. 6.

FIG. 8 shows the tubular segment of intestinal submucosa 40 folded back on itself to join its end portions 42, 44 to provide a first connective portion 46 to be attached, for instance, to a first bone and also to provide a bend indicated at 48 in the intermediate portion of the segment 40 to provide a second connective portion to be attached to a second bone articulated with respect to the first bone. The segment arrangement in FIG. 8, therefore, illustrates a method of using a double segment or multilayered segment of intestinal submucosa tissue in accordance with this invention.

FIG. 9 illustrates another method in which a segment 60 of intestinal submucosa is pulled within another tubular segment 62 of intestinal submucosa to provide a dual segment or double segment arrangement having greater strength.

Presently, it is believed that forming the present grafts to have the stratum compactum layer of the intestinal submucosa internally, at least in the intermediate portion, will promote graft vascularization, and tests have been made to establish this fact. It should be recognized, however, that having the stratum compactum on the exterior may function likewise to allow or even promote graft vascularization, and future tests may establish this fact. For instance, it will be appreciated that the arrangement shown in FIGS. 5, 6 and 7, the multiwrap arrangement, is such that the stratum compactum of the outer wrap is against the tunica submucosa of the inner wrap.

The grafts may be sterilized using some conventional sterilization techniques including glutaraldehyde tanning with glutaraldehyde, formaldehyde tanning at acidic pH, propylene oxide treatment, gamma radiation, and peracetic acid sterilization. A sterilization technique which does not significantly weaken the mechanical strength and mechanical properties of the graft is preferably used. For instance, it is believed that strong gamma radiation may cause loss of strength in the graft material. Because one of the most attractive features of these intestinal submucosa grafts is the host-remodelling responses, it is desirable not to use a sterilization approach which will detract from that property.

It is presently believed that a suitable graft material should have a uniaxial longitudinal tensile strength of at least 3.5 MPa and a strain of no more than 20% with maximal load; a burst point of at least 300 mmHg for a specimen that is originally 100 microns thick and shaped in a tube of approximately 3 mm internal diameter; and a porosity that is between 0.5 and 3.0 ml at 120 mmHg pressure per square centimeter. As indicated above, it is presently believed that the most available appropriate source for such intestinal submucosa graft may be the small intestine from 400 to 600 lb. sows which are harvested in slaughter houses. The tubular segments from such sows typically have a diameter of about 10 mm to about 15 mm.

The graft material has a characteristic stress-strain relationship. Because orthopedic application of the graft construct will most often involve stress upon the graft, it is desirable that the graft material be "pre-conditioned" by controlled stretching prior to use as a connective tissue replacement.

One method of "pre-conditioning" involves application of a given load to the intestinal submucosa graft material for three to five cycles. Each cycle consists of applying a load of approximately two megapascals to the graft material for five seconds, followed by a ten second relaxation phase. It has been found that three to five cycles causes approximately twenty percent strain. The graft material does not return to its original size; it remains in a "stretched" dimension.

To date, several studies have been made that relate to orthopaedic applications of the type described above in connection with the drawings using intestinal submucosa harvested from sows. These studies include 14 dogs in which intestinal submucosa has been implanted as an anterior cruciate ligament, six dogs in which intestinal submucosa has been implanted as a medial collateral ligament and nine dogs in which intestinal submucosa has been used as an achilles tendon. In a separate single animal, intestinal submucosa has been used as a "fracture wrap". Some of these animals have been euthanized and the grafts harvested for evaluation.

Results of three dogs with anterior cruciate ligament replacements have been evaluated to show that the tensile strength of the intestinal submucosa graft was at least 70% of the contralateral normal anterior cruciate ligament (ACL) by 10 weeks post-surgery. These evaluations show that the graft was approximately three times the thickness at 10 weeks than it was at the time of the implantation, and it was well vascularized. The intestinal submucosa ACLs also become covered with synovium within two to three weeks and incorporate into the bone through the bone tunnels extremely rapidly and strongly. The longest survivors at this time are approximately eight months and appear to be doing well.

Two dogs with the intestinal mucosa medial collateral ligament have also been sacrificed to show aggressive fibroblastic ingrowth at one month post-surgery with synovial lining of the articular surface. The graft is attached firmly to the extra-articular aspect of the medial meniscus. There was almost complete restoration of medial stability of the knee within four weeks of implantation. At this time, the remaining five dogs with intestinal submucosa medial collateral ligaments are clinically normal with no instability.

Three dogs with achilles tendon replacements with intestinal submucosa have been sacrificed. Of the three groups of dogs, this group showed the most visible evidence of graft remodelling (probably because of location). The grafts thicken to the normal achilles tendon thickness within approximately four to six weeks and can support the normal weight of the animal without a brace within one month. The remodelled connective tissue shows extensive vascularization and orientation of the collagen fibrils along the lines of stress. The only inflammation that was present was represented by small accumulations of mononuclear cells near the suture material, just as would be seen in any surgical wound. The intestinal submucosa grafts appear to develop a peritenon that is synovialized and the boundary between the normal achilles and the intestinal submucosa graft was no longer recognizable with H&E stained histologic tissue sections by 16 weeks post-surgery. Six dogs remain to be sacrificed in this group and the longest survivor is now approximately six months post-implant.

The bone tunnels with the encompassed intestinal submucosa grafts have never been shown to be the weak point in tensile strength evaluations after sacrifice of dogs that have had the intestinal submucosa ACL surgery. In addition, the test animals have not had any infection problem with any of the orthopaedic applications to date.

What is claimed is:

1. A tendon or ligament graft construct for use as connective tissue substitute, said graft formed from a segment of intestinal tissue of a warm-blooded vertebrate, said segment comprising the tunica submucosa, the muscularis mucosa, and the stratum compactum of the tunica mucosa, said tunica submucosa, muscularis mucosa and stratum compactum being delaminated from the tunica muscularis and the luminal portion of the tunica mucosa of said segment of intestinal tissue, said graft construct having an intermediate portion and opposite end portions, said end portions being formed to present multiple segment layers for providing reinforcement for attachment of the graft construct to existing physiological structures, said graft construct further being conditioned for its use as a connective tissue substitute by stretching so that the graft construct is longer than the segment of intestinal tissue from which it is formed.

2. The graft construct of claim 1 conditioned by stretching so that it is about 10 to about 20 percent longer than the intestinal segment from which it was formed.

3. The graft construct of claim 1 in which said segment is folded back on itself to join said end portions to provide a first connective portion to be attached to a first physiological structure and a bend in said intermediate portion to provide a second connective portion to be attached to a second physiological structure.

4. The graft construct of claim 1 in which one of said end portions is adapted to be attached to a first bone and the other of said end portions is adapted to be attached to a second bone articulated with respect to said first bone, said construct being conditioned by stretching so that it is longer than the segment of intestinal tissue from which is was formed so that it can be placed under tension between said first and second bones to provide a ligament function.

5. A tendon or ligament graft for use as a connective tissue substitute in both ligament and tendon locations throughout the body, said graft comprising intestinal tissue of a warm-blooded vertebrate, said segment comprising the tunica submucosa, the muscularis mucosa and the stratum compactum of the tunica mucosa, said tunica submucosa, muscularis muscosa and stratum compactum being delaminated from the tunica muscularis and the luminal portion of the tunica mucosa of said segment of intestinal tissue, said graft being formed to have an intermediate portion comprising multiple tissue segment layers, said intermediate portion terminating with opposite end portions, said end portions being formed for attachment to a bone, tendon or ligament, said graft further being conditioned for use as a tendon or ligament substituted by stretching so that the graft is longer than the segments of intestinal tissue from which it is formed.

6. The graft of claim 5 conditioned by stretching longitudinally so that it is about 10 to about 20 percent longer than the segment of intestinal tissue from which it was formed.

7. The graft of claim 5 conditioned by stretching laterally so that it is wider than the segment of intestinal tissue from which it is formed.

8. The graft of claim 5 in which said segment is cut and flattened out to provide an elongated sheet extending in the longitudinal direction of the intestine to have generally parallel sides and opposite ends, said sheet being rolled up about generally a cylindrical axis generally perpendicular to the longitudinal direction to provide said intermediate portion to encose a tendon or ligament, said sides providing said opposite end portions to be attached to said enclosed tendon or ligament on opposite sides of a break or tear therein.

9. The graft of claim 8 in which said sheet is rolled up to have multilayers of said segment for enclosing a ligament or tendon.

10. The graft of claim 1 in which said graft is formed with at least two such segments, one pulled within the other to provide a double walled tubular structure with the adjacent end portions joined together.

11. A tendon or ligament graft material formed from a segment of intestinal tissue, said graft material comprising the tunica submucosa, the muscularis mucosa and the stratum compactum of the tunica mucosa, said tunica submucosa, muscularis mucosa and stratum compactum being delaminated from the tunica muscularis and the luminal portion of the tunica mucosa of said segment of intestinal tissue, and said graft material initially having a longitudinal dimension corresponding to the length of the segment of intestinal tissue and a lateral dimension proportioned to the diameter of the segment of intestinal tissue, said tissue graft material being stretched longitudinally so that it is longer than the segment of intestinal tissue from which it was formed.

12. The tendon or ligament graft material of claim 11 stretched to a length about 10 to about 20% longer than the segment of intestinal segment from which it was formed.

13. The tendon or ligament graft material of claim 11 wherein the tissue graft material is also stretched laterally.

* * * * *